United States Patent [19]

Gandour et al.

[11] Patent Number: 5,196,418

[45] Date of Patent: Mar. 23, 1993

[54] HEMICHOLINIUM LIPIDS AND USE THEREOF

[75] Inventors: Richard D. Gandour; Gnanasambandam Kumaravel, both of Baton Rouge, La.

[73] Assignee: Board of Supervisors, Louisiana State University Agricultural & Mechanical College, Baton Rouge, La.

[21] Appl. No.: 837,360

[22] Filed: Feb. 14, 1992

[51] Int. Cl.$^5$ .................. A61K 31/535; C07D 265/30; C07D 265/32
[52] U.S. Cl. .................. 514/230.8; 544/158; 544/173; 564/292
[58] Field of Search .................. 544/158, 173; 514/230.8

[56] References Cited

U.S. PATENT DOCUMENTS 3,225,042  12/1965  Dillard et al. .................. 544/173
4,670,557  6/1987  Su .................. 544/178

OTHER PUBLICATIONS

Rekka et al., Chemical Abstracts, vol. 112 (1989) No. 35775q.
Lee et al., Chemical Abstracts, vol. 116 (1992) No. 250124q.
Gandour et al., Chemical Abstracts, vol. 110 (1988) No. 110640f.

Primary Examiner—Robert W. Ramsuer
Attorney, Agent, or Firm—Richard J. Hammond

[57] ABSTRACT

Compounds of the present invention are those having the formula:

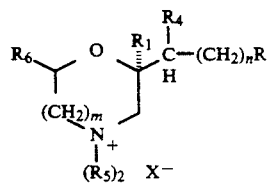

where R is a linear or branched chain of 1 to 22 carbon atoms selected from the group consisting of alkyl, alkenyl or alkynyl or said $C_1$ to $C_{22}$ chains substituted with $-SR_3$, $-OR_3$, $-NHR_3$, $-CH_3$, or $-C(O)OR_2$ where $R_2$ is hydrogen or $C_1$ to $C_6$ alkyl; $R_1$ is hydrogen, $C_1$ to $C_6$ alkyl, $-SR_3$, $-OR_3$, $-NHR_3$, $-NR'_3R_3$, or $-C(O)OR_2$ where $R_2$ is as previously defined; $R_3$ and $R'_3$ are the same or different and are hydrogen, $C_1$ to $C_6$ alkyl, alkylthioalkyl, alkoxyalkyl, aminoalkyl, aminoalkyl substituted with phenyl, substituted phenyl, benzoyl, substituted benzoyl, heteroaryl or substituted heteroaryl; $R_4$ is hydrogen, $C_1$ to $C_6$ alkyl, or $-C(O)OR_2$ where $R_2$ is defined previously; $R_5$ is hydrogen, $C_1$ to $C_6$ alkyl, phenyl, or substituted phenyl; $R_6$ is hydrogen, $C_1$ to $C_6$ alkyl, phenyl, substituted phenyl, heterroaryl or substituted heteroaryl; m is an integer from 0 to 3; and n is an integer from 1 to 23.

The compounds provide useful methods of inhibiting carnitine palmitoyltransferase.

12 Claims, No Drawings

HEMICHOLINIUM LIPIDS AND USE THEREOF

FIELD OF THE INVENTION

The invention relates to novel compounds useful as inhibitors for certain enzymatic-regulated lipid metabolites in eukaryotic cells. Specifically, this invention relates to certain hemicholinium compounds and methods for using such compounds as therapeutic agents.

BACKGROUND OF INVENTION (R)-Carnitine is a naturally occurring compound found in both plant and animal tissues. High concentrations are located in vertebrates' heart and muscle tissues, which depend heavily upon fatty acid oxidation as an energy source. Carnitine is a substrate of a class of enzymes, carnitine acyltransferases, that catalyze the reversible transfer of acyl groups between carnitine and acyl coenzyme A. Acylated carnitine acts as a carrier of fatty acyl groups across mitochondrial membranes in vectorial transport mediated by a translocase enzyme. Carnitine has proven useful in the treatment of myocardial ischemia in animals. It facilitates the transfer of fatty acids in damaged areas, hence increasing energy product and promoting survivability of the tissue. See Gandour, et al., Bioorganic Chem., 13, 197-208 (1985).

Hemiacetylcarnitinium (HAC) is a good inhibitor of carnitine acetyltransferase (CAT). This analog structurally resembles the hemicholiniums, which inhibit acetylcholine synthesis by blocking the uptake of choline and serve a substrates for choline acetyltransferase.

Hemipalmitoyl carnitinium (HPC) is a potent inhibitor of carnitine palmitoyltransferase (CPT), which is believed to be rate limiting for hepatic mitochondrial β-oxidation of long-chain fatty acids. CP activity usually increases under certain conditions, e.g., starvation and diabetes, resulting in higher levels of fatty-acid oxidation and ketogenesis. CPT inhibitors (e.g., 2-tetradecylglycidyl-CoA and amino- and palmitoylaminocarnitine) decrease blood ketone and blood glucose concentrations in vivo, suggesting that CPT inhibitors can aid in alleviating the diabetic syndrome.

Effective CPT inhibitors have certain moieties in common. Most have a long-chain alkyl group attached to either CoA or a carnitine analog. Illustrative of these inhibitors are: 2-bromopalmitoyl-CoA and -carnitine S-2-bromomyristoylthiocarnitine, 2-alkyl-2-glycidyl-carnitine and -CoA, (1-pyrenebutyryl)-carnitine and -CoA, S-heptadecyl-CoA and heptadecan-2-onyldethio-CoA, palmitoylaminocarnitine, and myristoylaminocarnitine. CPT recognizes molecules containing a long-chain alkyl and a trimethylammonium group (e.g., palmitoylcholine and N-hexadecylsulfobetaine). Aminocarnitine, also known as emeriamine, and methylglyoxal bis(guanylhydrazone) are the known small molecule inhibitors of CPT. Some of the above inhibitors, however, are only effective with certain preparations of CPT. Furthermore, the location of the binding site of malonyl-CoA, the physiological inhibitor of CPT, has not been conclusively demonstrated. In any case, HPC is the most potent synthetic reversible inhibitor of catalytic activity in purified CPT assayed to date. See Gandour, et al., Archives of Biochem. and Biophys., 267 (2), 515-520 (1988).

Accordingly, there is a need for more potent inhibitors of CPT.

DESCRIPTION OF THE PREFERRED EMBODIMENTS

In the compounds of the present invention, the following definitions apply:

A linear or branched chain of 1 to 22 carbon atoms means selected from the group consisting of alkyl means straight or branched chain alkyl having 1 to 22 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl (similarly, $C_1$ to $C_6$ alkyl means the above straight or branched alkyl groups having 1 to 6 carbon atoms in the chain).

Alkenyl means straight or branched chain alkenyl having 1 to 22 carbon atoms and at least one double bond and includes 1-propenyl, 1-butenyl, 1-pentenyl, 1-hexenyl, 1-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-eicosenyl, 1-docosenyl, 5,13-docosadienyl, etc.

Alkynyl means a straight or branched chain alkynyl having 1 to 22 carbon atoms and at least one triple bond and includes ethynyl, 1-propynyl, 1-butynyl, 1-pentynyl, 1-hexynyl, 1-heptynyl, 1-octynyl, 1-nonynyl, 1-decynyl, 1-undecynyl, 1-dodecynyl, 1-tridecynyl, 1-tetradecynyl, 1-pentadecynyl, 1-hexadecynyl, 1-heptadecynyl, 1-octadecynyl, 1-nonadecynyl, 1-eicosynyl, 1-docosynyl, 5,13-docosadiynyl, etc.

In the above illustrated alkenyl and alkynyl moieties, only a single point of unsaturation is shown. However, it should be understood that the unsaturated grouping can be at a different position in the carbon chain or include more than one point of unsaturation.

Substituted phenyl means phenyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy isobutoxy, secondary butoxy, tertiary butoxy, pentyloxy, isopentyloxy, hexyloxy, heptyloxy, octyloxy, nonyloxy and decyloxy, haloalkyl which means straight or branched alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Heteroaryl means 5 to 10 membered mono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl.

Substituted heteroaryl means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus.

Alkoxy means straight or branched chain alkoxy having from 1 to 8 carbon atoms and includes methoxy, ethoxy, n-propoxy, isopropoxy, butoxy, isobutoxy, pentyloxy, hexyloxy, heptyloxy, octyloxy, etc.

Haloalkyl means straight or branched chain alkyl having 1 to 10 carbon atoms which is substituted by at least one halogen as mentioned above.

Hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1-hydroxy-2-propyl, 2-hydroxypropyl, 2,3 dihydroxypropyl, 1,3-dihydroxy-2-propyl, etc.

Alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexyloxyoctyl, 8-octyloxyoctyl, etc.

Aminoalkyl means that the alkyl moiety is straight or branched chain alkyl having 1 to 8 carbon atoms and includes, for example, aminomethyl, 2-aminoethyl, 3-aminopropyl, 4-aminobutyl, 6-aminohexyl, 8-aminooctyl, etc.

Alkylthioalkyl means that the alkylthio moiety and the alkyl moiety each are straight or branched chain ones having 1 to 8 carbon atoms, and includes, for example, methylthiomethyl, ethylthiomethyl, propylthiomethyl, isopropylthiomethyl, butylthiomethyl, isobutylthiomethyl, tertiary butylthiomethyl, pentylthiomethyl, hexylthiomethyl, octylthiomethyl, 2-methylthioethyl, 2-ethylthioethyl, 2-butylthioethyl, 2-hexylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 4-butylthiobutyl, 6-methylthiohexyl, 6-ethylthiohexyl, 6-butylthiohexyl, 8-methylthiooctyl, 8-ethylthiooctyl, 8-butylthiooctyl, etc.

Alkanoyl means alkanoyl having 2 to 18 carbon atoms and includes, for example, acetyl, propionyl, butyryl, isobutyryl, pivaloyl, valeryl, hexanoyl, octanoyl, lauroyl, stearoyl, etc.

Substituted benzoyl means benzoyl which is substituted by at least one substituent selected from the group consisting of halogen, amino, nitro, hydroxy, alkyl, alkoxy and haloalkyl on the benzene ring.

The present invention embraces any of racemates and individual optical isomers thereof of the compounds of formula (I) having a chiral carbon atom.

The compounds of formula (I) are salts (where the counter ion is identified as $X^-$). As such, these salts include pharmaceutically acceptable salts such as where $X^-$ includes the inorganic acid addition salts (e.g., chloride, bromide, hydrochloride, hydrobromide, sulfate, nitrate or phosphate), organic acide addition salts (e.g., acetate, tartrate, citrate, fumarate, maleate, mandelate, oxalate, salicylate, hybenzate, fendizoate, methanesulfonate or p-toluenesulfonate), salts with bases (e.g., salt with triethylamine, diethanolamine, ammonium, guanidine, hydrazine, quinine or cinchoinin) or salts with amino acids (e.g., salt with lysine or glutamine).

The compounds of the present invention are those having the formula:

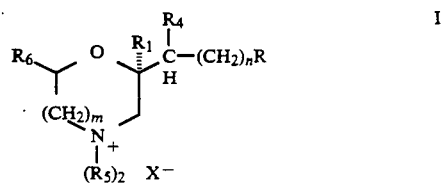

where R is $C_1$ to $C_{20}$ alkyl, substituted with $-SR_3$, $-OR_3$, $-NHR_3$, $-CH_3$, or $-C(O)OR_2$ where $R_2$ is hydrogen or $C_1$ to $C_6$ alkyl; $R_1$ is hydrogen, $C_1$ to $C_6$ alkyl, $-SR_3$, $-OR_3$, $-NHR_3$, $-NR'_3R_3$, or $-C(O)OR_2$ where $R_2$ is as previously defined; $R_3$ and $R'_3$ are the same or different and are hydrogen, $c_1$ to $c_6$ alkyl, alkythioalkyl, alkoxyalkyl, aminhoalkyl, aminoalkyl substituted with phenyl, substituted phenyl, benzoyl, substituted benzoyl, heteroaryl or substituted heteroaryl; $R_4$ is hydrogen, $C_1$ to $C_6$ alkyl, or $-C(O)OR_2$ where $R_2$ is defined previously; $R_5$ is hydrogen, $C_1$ to $C_6$ alkyl, phenyl, or substituted phenyl; $R_6$ is hydrogen, $C_1$ to $C_6$ alkyl, phenyl, substituted phenyl, heteroaryl or substituted heteroaryl; m is an integer from 0 to 3; and n is an integer from 1 to 23.

In the above compounds of formula I, it is preferred that R is $C_1$ to $C_{10}$ alkyl substituted with $-CH_3$ and n is 1 to 10. Most preferably, R is $C_1$ to $C_5$ alkyl substituted with methyl. Particularly preferred is where R is methylene substituted with methyl and n is 12.

In the case of $R_4$, it is preferred that this substituent is hydrogen or $C_1$ to $C_3$ alkyl; most preferably, hydrogen.

$R_1$ is preferably the group $-SR_3$ or $OR_3$. Most preferably, $R_1$ is $-OR_3$ where $R_3$ is hydrogen or $C_1$ to $C_6$ alkyl. Particularly preferred for $R_3$ groups are hydrogen or methyl.

Preferably, $R_6$ is hydrogen, $C_1$ to $C_6$ alkyl or phenyl; most preferably, hydrogen or $C_1$ to $C_3$ alkyl. Particularly preferred for $R_6$ is hydrogen.

In the compounds of formula I, $R_5$ is attached to the nitrogen atom and the remainder of the molecule completes the cationic form of these materials. As such, $R_5$ is preferably hydrogen or $C_1$ to $C_6$ alkyl; most preferably, $C_1$ to $C_3$ alkyl. Particularly preferred for $R_5$ is the group methyl.

As noted above, the anion associated with the cationic species is preferably the chloride or bromide; most preferably, the bromide. It should be understood, however, that the compounds of formula I can be in the free base form. In this free base compound, only a single $R_5$ group is attached to the nitrogen atom.

Especially preferred compounds of formula I are as follows: 2-hydroxy-4,4-dimethyl-2-octadecylmorpholinium bromide; 2-heptadecyl-2-hydroxy-4,4-dimethylmorpholinium bromide; 2-hexadecyl-2-hydroxy-4,4-dimethylmorpholinium bormide; 2-hydroxy-4,4-dimethyl-2-pentadecylmorpholinium boromide; 2-methoxy-4,4-dimethyl-2-pentadecylmorpholinium bromide; 2-hydroxy-4-methyl-2-pentadecylmorpholine; 2-hydroxy-4,4-dimethyl-2-tetradecylmorpholinium bromide; 2-hydroxy-4,4-dimethyl-2-tridecylmorpholinium bromide; 2-docecyl-2-hydroxy-4,4-dimethylmorpholinium brodmide; 2-decyl-2-hydroxy-4,4-dimethylmorpholinium bromide; and N-(3-hydroxypropyl)-N,N-dimethyl-N-(2-oxoheptaddecyl)ammonium bromide.

The compounds of formula I of the present invention can be prepared, for example, by treating an alkyl- or dialkyl-substituted amino-aliphatic alcohol, e.g., 2-(N,N-dimethyl-amno)ethanol, with a bromomethylketone as follows:

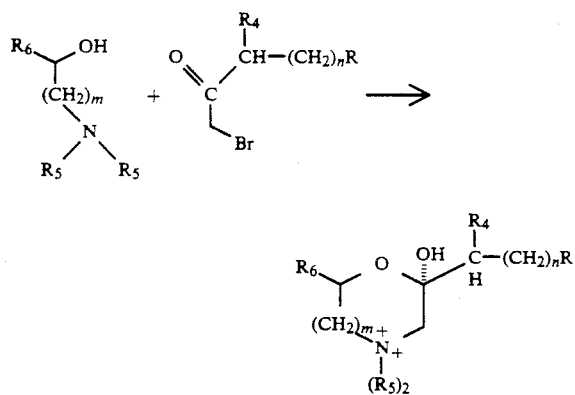

Typically, these reactions are carried out in highly polar solvents, such as dimethylsulfoxide, dimethylformamide or nitromethane, at temperatures from 25° C. to 100° C.

It should be noted that the compounds of formula I, sometimes called hemicholiniums, can exist in cyclic or in open chain form. In solution, a ring-chain tautomerism exists, illustrated by the following:

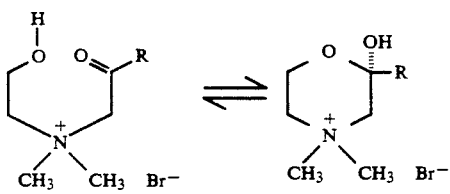

Thus, the compounds of formula I of the present invention includes the tautomers shown in the above illustrative equation.

The compounds of formula I where $R_1$ is:

1) hydrogen can be prepared in three steps: a) treating an epoxide with an aminoalcohol to produce an aminodiol; b) treating the aminodiol with tosyl chloride, then base, to yield the corresponding morphine; and c) treating the morphine with $R_5X$ giving a morpholinium salt as follows:

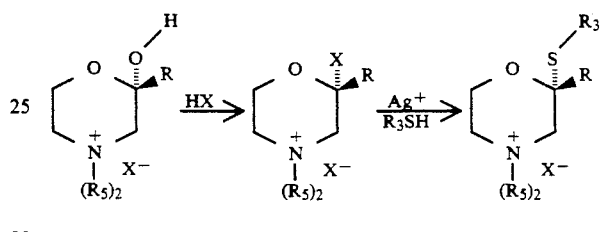

2) $-SR_3$ can be prepared by treating I ($R_1=OH$) with HX, then with $R_3SH$ as follows:

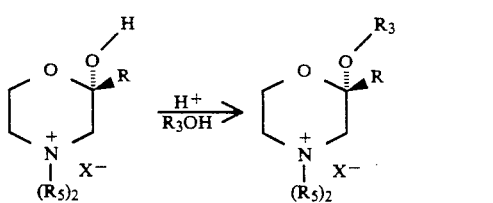

3) $OR_3$ can be prepared by treating I ($R_1=OH$) with $H^+$ and $R_3OH$ as follows:

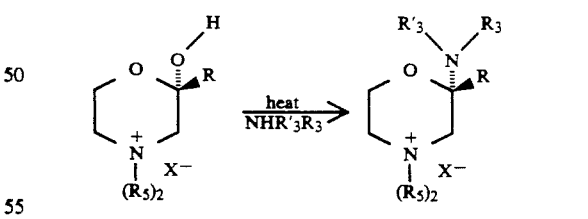

4) $-NR'_3R_3$ can be prepared by heating I ($R_1=OH$) with $NHR'_3R_3$ as follows:

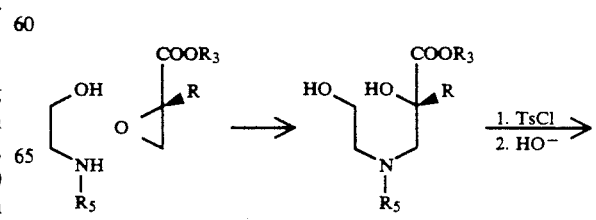

5) $-COOR_3$ can be prepared by a reaction sequence similar to that described in 1) as follows:

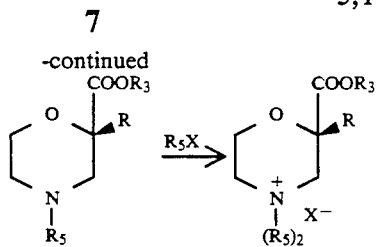

6) —CH₃ can be prepared by a reaction sequence similar to that described in 1) as follows:

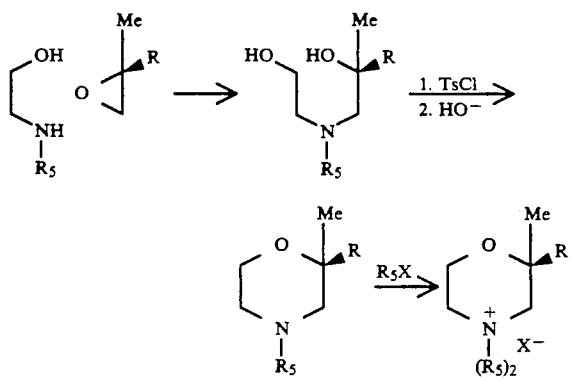

The bromomethylketones shown in the equation above are prepared by oxidation of α-olefins with NBS and Jones reagent in aqueous acetone using the procedure of Zaylyalov et al., *Bull. Acad. Sci.*, USSR (English Translation) 1989, 2152-2154, incorporated herein by reference.

The salts of the compounds of formula I are obtained in the course of the preparation of the compounds of formula I, where $R_5$ is di(alkyl, phenyl or substituted phenyl), by treating the above-mentioned pharmaceutically acceptable acid addition salts with an alkali, a base or an amino acid in a conventional manner. Where one of $R_5$ is hydrogen, the free base is obtained directly. Where $R_5$ is not hydrogen, the compounds typically remain in salt form.

The compounds of formula I of the present invention thus obtained can be separated by employing a conventional separation and purification procedure such as extraction, concentration, neutralization, filtration, recrystallization, column chromatography or thin layer chromatography from the reaction mixture.

The compounds of formula I having an asymmetric carbon are usually formed as racemates. These racemates can be separated into the individual optical isomers by, for example, forming salts with an optically active acid (e.g., mandelic acid, tartaric acid, dibenzoyltartaric acid or 10-camphorsulfonic acid) or an optically active base (e.g., cinchonine, cinchonidine, quinine, quinidine, α-methylbenzylamine or dehydroabiethylamine), or by separating with chromatography or fractional recrystallization. The optically active isomers can also be prepared directly by using optically active starting compounds.

EXAMPLES

General Procedure for the Preparation of Hemicholinium

To a stirred suspension of the appropriate bromomethyl ketone (6.9 mmol, 1 eq) in nitromethane (25 mL) was added 2-(N,N-dimethylamino)ethanol (10.36 mmol, 1.5 eq) and stirred at 50°-55° C. for 3 h. After cooling to room temperature, nitromethane was removed by rotary evaporation and the residue was treated with ethyl acetate. The precipitate formed was filtered and washed with ethyl acetate. The product was purified by recrystallizing from ethyl acetate and methylene chloride.

The hemicholiniums of Examples 1-8 have the following structure:

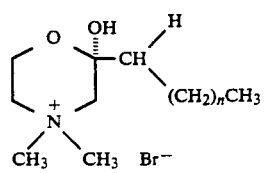

They are prepared using the General Procedure set forth above. The following illustrative compounds are prepared in this manner.

EXAMPLE 1

2-Hydroxy-4,4-dimethyl-2-octadecylmorpholinium Bromide, II, n=16

Yield 20%. ¹H NMR (DMSO-d₆, 200 MHz) δ0.85 (3H, t, CH₂-C$\underline{H}_3$), 1.24 (32H, s, CH₃-(CH₂)₁₆), 1.55 (2H, m, C₁₇H₃₅—C$\underline{H}_2$), 3.14 (3H, N—CH$_{3eq}$), 3.18-3.47 (4H, m), 3.31 (3H, s, N—CH$_{3ax}$), 3.81 (1H, m), 4.21 (1H, m), 6.42 (1H, s, OH); ¹³C NMR (DMSO-d₆, 50 MHz) δ 94.4, 63.7, 59.4 56.9 53.9 49.9 31.3, 29.0, 28.7, 22.3, 22.1, 13.9, IR (KBr) 3174, 2920, 2851, 1468, 1162, 1090, 980, 657, 586. Anal. Calcd. for C₂₄H₅₀NO₂Br: C, 62.07; H, 10.78; N, 3.02, Found: C, 62, 6; H, 10.77; N, 2.95.

EXAMPLE 2

2-Heptadecyl-2-hydroxy-4,4-dimethylmorpholinium Bromide, II, n=15

Yield 68%. ¹H NMR (CDCl₃, 200 MHz) δ 0.88 (3H, t, CH₂—C$\underline{H}_3$), 1.25 (28H, s, CH₃—(C$\underline{H}_2$)₁₄), 1.39 (2H, m, C₁₅H₃₁—C$\underline{H}_2$), 1.73 (2H, m, C₁₆H₃₃—C$\underline{H}_2$), 2.55 (t, Open form), 3.19 (1H, d), 3.37-4.03 (4H, m), 3.49 (3H, s, N—CH$_{3eq}$), 3.55 (s, N—CH₃ open form), 3.74 (3H, s, N—CH$_{3ax}$), 4.50 (1H, m), 5.11 (1H bs, OH); ¹³C NMR (CDCl₃, 50 MHz) δ 95.00, 65.39, 60.86, 58.65, 54.94, 51.38, 40.73, 31.91, 29.72, 29.36, 22.68, 22.49, 14.09; IR (KBr) 3164, 2919, 2850, 1469, 1164, 980, 662.

EXAMPLE 3

2-Hexadecyl-2-hydroxy-4,4-dimethylmorpholinium Bromide, II, n=14

Yield 55%. ¹H NMR (DMSO-d₆, 200 MHz) δ 0.85 (3H, t, CH₂—C$\underline{H}_3$), 1.24 (28H, s, CH₃-(C$\underline{H}_2$)14), 1.55 (2H, m, C₁₅H₃₁—C$\underline{H}_2$), 3.15 (3H, s, N—CH$_{3eq}$), 3.19-3.47 (4H, m), 3.31 (3H, s, N—CH$_{3ax}$), 3.81 (1H, m) 4.21 (1H, m), 6.42 (1H, s, OH); ¹³C NMR (DMSO-d₆, 50 MHz) δ 94.36, 63.64, 59.40, 56.89, 53.92, 49.86, 31.26, 29.02, 28.67, 22.30, 22.07, 13.92; IR (KBr) 3175, 2919, 2852, 1468, 1343, 1163, 10 91, 981, 657, 586. Anal. Calcd. for C₂₂H₄₆NO₂Br: C, 60.55; H, 10.55; N, 3.21. Found: c, 60.55, H, 10.56, N, 3.19.

EXAMPLE 4

2Hydroxy-4,4-dimethyl-2-pentadecylmorpholinium Bromide, II, n=13

Yield 67%. ¹H NMR (CDCl₃, 200 MHz) δ 0.88 (3H, t, CH₂—C$\underline{H}_3$), 1.25 (24H, CH₃-(C$\underline{H}_2$)₁₂), 1.39 (2H, m, C₁₃H₂₇-C$\underline{H}_2$), 1.79 (4H, m, C₁₄H₂₉-C$\underline{H}_2$ and H₂O), 2.55 (t, open form), 3.19 (1H, d), 3.44 (1$\overline{\text{H}}$, m), 3.50 (3H, s, N—CH$_{3eq}$), 3.56 (s, N—CH₃, open form), 3.76 (3H, s, N—CH$_{3ax}$), 3.92 (2H, m), 4.02 (1H, m), 4.49 (1H, m), 4.88 (1H bs, OH), 5.16 (s, from open form); $^{13}$C NMR (CDCl$_3$, 50 MHz) δ 95.01, 65.26, 60.72, 58.50, 54.92, 51.28, 40.73, 31.87, 29.69, 29.32, 22.62, 14.05; IR (KBr) 3531, 3371, 3242, 3169, 2919, 2849, 1641, 1470, 1223, 1082, 941. Anal. Calcd. for C$_2$H$_{44}$NO$_2$BrH$_2$O: C, 57.27; H, 10.45; N, 3.18. Found: C, 57.36, H, 10.32, N, 3.13.

EXAMPLE 5

2-Hydroxy-4,4-dimethyl-2,-tetradecylmorpholinium Bromide, II, n=12

Yield 69%. $^1$H NMR (CDCl$_3$, 200 MHz) δ 0.88 (3H, t, CH$_2$—CH$_3$), 1.25 (22H, CH$_3$-(CH$_2$)$_{11}$), 1.40 (2H, m, C$_{12}$H$_{25}$-C$\overline{H}_2$), 1.77 (2H, m, C$_{13}$H$_{27}$-C$\overline{H}_2$), 2.56 (t, open fomr), 3.20 (1H, d), 3.44 (1H, m), 3.51 (3H, s, N-CH$_{3eq}$), 3.55 (s, N—CH$_3$ open form), 3.77 (3H, s, N—CH$_{3ax}$), 3.97 (3H, m), 4.50 (1H, m), 4.68 (1H, bs, OH), 5.18 (s, from open form); $^{13}$C NMR (CDCl$_3$, 50 MHz) δ 95.0, 65.44, 60.92, 58.73, 54.86, 51.43, 40.68, 31.93, 29.68, 29.52, 29.37, 22.68, 22.32, 14.12; IR (KBr) 3151, 2917, 2851, 1468, 1343, 1229, 1162, 1090, 980, 656, 585. Anal. Calcd. for C$_{20}$H$_{42}$NO$_2$Br: C, 58.82; H, 10.29; N, 3.43. Found: C, 58.79, H, 10.27, N, 3.43.

EXAMPLE 6

2-Hydroxy-4,4-dimethyl-2-tridecylmorpholinium Bromide, II, n=11

Yield 62%. $^1$H NMR (CDCl$_3$, 200 MHz) δ 0.88 (3H, t, CH$_2$—CH$_3$), 1.25 (20H, CH$_3$-(CH$_2$)$_{10}$), 1.40 (2H, m, C$_{11}$H$_{23}$—C$\overline{H}_2$), 1.78 (2H, m, C$_{12}$H$_{25}$-C$\overline{H}_2$), 2.0 (2H, s, H$_2$O), 2.6 (t, open form), 3.19 (1H, d), 3.44 (1H, m), 3.50 (3H, s, N—CH$_{3eg}$), 3.56 (s, N—CH$_3$ open form), 3.76 (3H, s, N—CH$_{3ax}$), 3.87-4.06 (3H, m), 4.50 (1H, m), 4.87 (1H, bs, OH), 5.14 (s, from open form); $^{13}$C NMR (CDCl$_3$, 50 MHz) δ 94.98, 5.20, 60.64, 58.41, 54.82, 51.17, 40.66, 31.82, 29.62, 29.26, 22.57, 14.00; IR (KBr) 3530, 3367, 3241, 3167, 2919, 2850, 1641, 5 1470, 1229, 1082, 976, 803. Anal. Calcd. for C$_{19}$H$_{40}$NO$_2$Br: C, 57.86; H, 10.15; N, 3.55. Found: C, 57.61, H, 10.17, N, 3.47.

EXAMPLE 7

2-Dodecyl-2-hydroxy-4,4-dimethylmorpholinium Bromide, II, n=10

Yield 65%. $^1$H NMR (CDCl$_3$, 200 MHz) δ 0.88 (3H, t, CH$_2$—CH$_3$), 1.25 (18H, CH$_3$-(CH$_2$)$_9$), 1.40 (2H, m, C$_{10}$H$_{21}$—CH$_2$), 1.77 (2H, m, C$_{11}$H$_{23}$-C$\overline{H}_2$), 2.55 (t, open form), 3.20 (1H, d), 3.44 (1H, m), 3.51 (3H, s, N—CH-$_{3eg}$), 3.57 (s, N—CH$_3$ open form), 3.76 (3H, s, N—CH-$_{3ax}$), 3.87-4.21 (3H, m), 4.50 (1H, m), 5.09 (1H, bs, OH), 5.16 (s, from open form); $^{13}$C NMR (CDCl$_3$, 50 MHz) δ 95.05, 65.39, 60.83, 58.60, 54.90, 51.34, 40.73, 31.91, 29.66, 29.36, 22.68, 22.54, 14.11; IR (KBr) 3174, 2921, 2852, 1468, 1343, 1236, 1162, 1090, 981, 918, 657. Anal. calcd, for C$_{18}$H$_{38}$NO$_2$Br: C, 56.84; H, 10.00; N, 3.68. found: C, 56.89, H, 10.01, N, 3.67.

EXAMPLE 8

2-Decyl-2-hydroxy-4,4-dimethylmorphlinium Bromide, II, n=8

Yield 45%. $^1$H NMR (CDCl$_3$, 200 MHz) δ 0.88 (3H, t, CH$_2$—CH$_3$), 1.25 (14H, CH$_3$-(CH$_2$)$_7$), 1.40 (2H, m, C$_8$H$_{17}$—C$\overline{H}_2$), 1.77 (2H, m, C$_9$H$_{19}$-C$\overline{H}_2$), 2.55 (t, open form), 3.20 (1H, d), 3.44 (1H, m), 3.51 (3H, s, N—CH-$_{3eq}$), 3.57 (s, N—CH$_3$ open form), 3.76 (3H, s, N—CH-$_{3ax}$), 3.91 (2H, m), 4.05 (1H, m), 4.50 (1H, m), 4.98 (1H, bs, OH; $^{13}$C NMR (CDCl$_3$, 50 MHz) δ 95.01, 65.24, 60.67, 58.44, 54.80, 51.19, 40.65, 31.80, 29.55, 29.26, 22.57, 14.01; IR (KBr) 3402, 3173, 2921, 2853, 1468, 1343, 1249, 1162, 1089, 1052, 979, 924, 657. Anal. Calcd, for C$_{16}$H$_{34}$NO$_2$Br: C, 54,54; H, 9.73; N, 3.98. Found: C, 54.47, H, 9.68, N, 3.91.

An example of the tautermeric fomr of the compounds of formula I is shown in Example 9.

EXAMPLE 9

N-(3-Hydroxypropyl)-N,N-dimethyl-N-(2-oxoheptadecyl)ammonium Bromide

Yield 54%. $^1$H NMR (CDCl$_3$, 200 MHz) δ 0.88 (3H, t, CH$_2$—CH$_3$), 1.25 (22H, CH$_3$—(CH$_2$)$_{11}$), 1.59 (2H, m, C$_{12}$H$_{25}$—C$\overline{H}_2$), 2.1 (2H, m), 3.07 (2$\overline{H}$, m), 4.24 (1H, bs, OH), 5.08 (2H, s, NCH$_2$CO); $^{13}$C NMR (CDCl$_3$ 50 MHz) δ 67.89, 64.35, 58.30, 51.42, 51.19, 41.43, 31.88, 29.66, 29.44, 29.0, 26.09, 22.83, 22.64, 14.04; IR (KBr) 3316, 2916, 1850, 1732, 164, 1480, 1411, 1074, 918, 609. Anal. Calcd. for C$_{22}$H$_{46}$NO$_2$Br: C, 60.55; H, 10.55; N, 3.21. Found: C, 60.30, H, 10.82, N, 3.18.

The following are the results pharmacological experiments exhibiting the effectiveness of the compounds (I), or their salts, of the present invention.

CPT Inhibition

Methods

Preparation: CPT-II was prepared from beef liver using the methods of P. R. H. Clarke and L. L. Bieber (1981) *J. Biol. Chem.*, 256. 9861-9868.

In final volume of 1 ml, 20 mm KPO$_4^-$, pH 7.4 at 30° C., 125 μM aldrithiol [4,4-dithio(bis)pyridine], 10 μM decanoyl-CoA, 10 μl enzyme (1.25 μg/ml) and inhibitor were preincubated at 30° C. for 1 min. and the reaction was initiated with L-carnitine. The absorbance change at 324 nm, followed in a spectrophotometer, was linear with time. L-carnitine conc. were 1 mM and 5 mM. H15C conc. ranged from 1.25 μM-12.5 μM (6values).

Results

K$_i$ for H$_{15}$C (Example 4) is 2 μM.

Assays of these compounds against CPT provides evidence that these are potential inhibitors of CPT. For example, the compound of Example 4 has a K$_i$ value of 2 μM, which indicates a five-fold stronger binding than palmitoylcholine, which has a K$_i$ of 10.4 μM against CPT.

Inhibition of Cell-Cell Aggregation

Cell-cell aggregation studies by the method of Fritz et al., J. Cell. *Physiol.*, 149, 269-276 (1991), show that hemicholinium lipids:

H16C = 2-hexadecyl-2-hydroxy-4,4-dimethylmorpholinium bromide;
H15C = 2-hydroxy-4,4-dimethyl-2-pentadecylmorpholinium bromide;
H4C = 2-hydroxy-4,4-dimethyl-2-tetradecylmorpholinium bromide;
H12C = 2-dodecyl-2-hydroxy-4,4-dimethylmorpholinium bromide; and
AK-15 = N-(3-hydroxypropyl)-N,N-dimethyl-N-(2-oxoheptadecyl)-ammonium bromide are effective inhibitors.

| Compound | K$_i$ |
| --- | --- |
| H16C (Example 3) | 400 nM |
| H15C (Example 4) | 400 nM |
| H14C (Example 5) | 1.5 μM |
| H12C (Example 7) | 12 μM |

-continued

| Compound | $K_i$ |
|---|---|
| AK-15 (Example 9) | 750 nM |

These hemicholinium compounds are also inhibitors of those biological functions where a lipid and a choline structure are required for activity. They are also surfactant biocides, inhibitors of protein kinase C, and male contraceptives.

When the compounds of the present invention or the pharmaceutically acceptable salts thereof are used as drugs, they can be orally or parenterally administered alone or in the form of powder, granules, tablets inclusive of film-coated tablets and sugar coated tablets, capsules, injections, drip infusions, suppositories, ointments, cataplasms or eye drops prepared by admixing with pharmaceutically acceptable carriers, vehicles or diluents to patients in need of therapy. The dose may vary depending upon the disease to be treated, the conditions of patient, the age of patient or way of administration, and in case of oral administration, the daily does for human adults ranges from 1 to 1,000 mg, preferably from 50 to 500 mg, in one to several times divided doses.

We claim:

1. An optically active or racemic mixture of a compound of the formula:

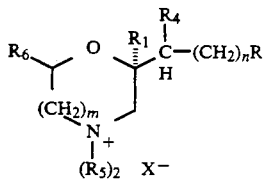

where R is a linear or branched chain of 10 to 22 carbon atoms selected from the group consisting of alkyl, alkenyl or alkynyl or said $C_{10}$ to $C_{22}$ chains substituted with —$SR_3$, —$OR_3$, —$NHR_3$, —$CH_3$, or —$C(O)OR_2$ where $R_2$ is hydrogen or $C_1$ to $C_6$ alkyl;

$R_1$ is —$SR_3$ or —$OR_3$;

$R_3$ is hydrogen, $C_1$ to $C_6$ alkyl, alkylthioalkyl, alkoxyalkyl, aminoalkyl, aminoalkyl substituted with phenyl, substituted phenyl, benzoyl, substituted benzoyl, heteroaryl or substituted heteroaryl;

$R_4$ is hydrogen, $C_1$ to $C_6$ alkyl, or —$C(O)OR_2$ where $R_2$ is defined previously;

$R_5$ is hydrogen, $C_1$ to $C_6$ alkyl, phenyl, or substituted phenyl;

$R_6$ is hydrogen, $C_1$ to $C_6$ alkyl, phenyl, substituted phenyl, heteroaryl or substituted heteroaryl;

m is 1;

and n is an integer from 1 to 23.

2. The compound of claim 1 wherein $R_4$ is hydrogen.

3. The compound of claim 1 wherein R is $C_{10}$ to $C_{20}$ alkyl substituted with $CH_3$.

4. The compound of claim 2 wherein n is an integer of from 1 to 14.

5. The compound of claim 3 wherein $R_1$ is —$OR_3$ is hydrogen or $C_1$ to $C_6$ alkyl.

6. The compound of claim 5 wherein $R_3$ is hydrogen or methyl.

7. The compound of claim 3 wherein $R_6$ is hydrogen, $C_1$ to $C_6$ alkyl or phenyl.

8. The compound of claim 7 wherein $R_6$ is hydrogen.

9. The compound of claim 7 wherein $R_5$ is hydrogen or $C_1$ to $C_6$ alkyl.

10. The compound of claim 9 wherein $R_5$ is $C_1$ to $C_3$ alkyl.

11. The compound of claim 10 wherein X is a pharmaceutically acceptable inorganic acid addition salt.

12. A method for inhibiting the enzyme carnitine palmitoyltransferase in mammals comprising treating said mammals with an effective amount of a compound according to claim 1.

* * * * *